(12) United States Patent
Raveendran-Nair et al.

(10) Patent No.: US 10,583,407 B2
(45) Date of Patent: Mar. 10, 2020

(54) REDUCED GRAPHENE OXIDE BARRIER MATERIALS

(71) Applicant: The University of Manchester, Manchester (GB)

(72) Inventors: Rahul Raveendran-Nair, Manchester (GB); Yang Su, Manchester (GB); Andre Geim, Cambridge (GB)

(73) Assignee: The University of Manchester, Manchester (GB)

( * ) Notice: Subject to any disclaimer, the term of this patent is extended or adjusted under 35 U.S.C. 154(b) by 449 days.

(21) Appl. No.: 15/129,152

(22) PCT Filed: Mar. 26, 2015

(86) PCT No.: PCT/GB2015/050900
§ 371 (c)(1),
(2) Date: Sep. 26, 2016

(87) PCT Pub. No.: WO2015/145155
PCT Pub. Date: Oct. 1, 2015

(65) Prior Publication Data
US 2017/0106342 A1    Apr. 20, 2017

(30) Foreign Application Priority Data

Mar. 28, 2014 (GB) .................................. 1405642.8
May 2, 2014 (GB) .................................. 1407851.3

(51) Int. Cl.
*C01B 32/182* (2017.01)
*B01D 71/02* (2006.01)
(Continued)

(52) U.S. Cl.
CPC ....... *B01D 71/021* (2013.01); *B01D 67/0044* (2013.01); *B01D 71/024* (2013.01);
(Continued)

(58) Field of Classification Search
CPC .......................... B01D 71/021; B01D 71/024; B01D 67/0044; C01B 32/182; C01B 32/23;
(Continued)

(56) References Cited

U.S. PATENT DOCUMENTS

2009/0235721 A1  9/2009  Robinson et al.
2011/0189452 A1  8/2011  Lettow et al.
(Continued)

FOREIGN PATENT DOCUMENTS

CN    101812194 A    8/2010
CN    102040217 A    5/2011
(Continued)

OTHER PUBLICATIONS

An et al., "Bio-Inspired Borate Cross-Linking in Ultra-Stiff Graphene Oxide Thin Films," Advanced Materials, Sep. 1, 2011, vol. 23, No. 33, pp. 3842-3846.
(Continued)

*Primary Examiner* — Taiwo Oladapo
(74) *Attorney, Agent, or Firm* — Wilmer Cutler Pickering Hale and Dorr LLP

(57) ABSTRACT

This invention relates to barrier materials comprising reduced graphene oxide, methods of making said materials and their uses. The reduced graphene oxide is preferably formed from the reduction of graphene oxide by HI, HBr or ascorbic acid.

22 Claims, 4 Drawing Sheets

(51) Int. Cl.
| | |
|---|---|
| G01N 15/08 | (2006.01) |
| C01B 32/23 | (2017.01) |
| B01D 67/00 | (2006.01) |
| B32B 37/12 | (2006.01) |
| B32B 37/14 | (2006.01) |
| B82Y 30/00 | (2011.01) |
| B82Y 40/00 | (2011.01) |

(52) U.S. Cl.
CPC .............. *B32B 37/12* (2013.01); *B32B 37/14* (2013.01); *C01B 32/182* (2017.08); *C01B 32/23* (2017.08); *G01N 15/082* (2013.01); *B82Y 30/00* (2013.01); *B82Y 40/00* (2013.01); *G01N 2015/086* (2013.01); *Y10S 977/734* (2013.01); *Y10S 977/847* (2013.01)

(58) Field of Classification Search
CPC ...... B32B 37/12; B32B 37/14; G01N 15/082; G01N 2015/086; Y10S 977/847; Y10S 977/734; B82Y 30/00; B82Y 40/00
See application file for complete search history.

(56) References Cited

U.S. PATENT DOCUMENTS

| | | | |
|---|---|---|---|
| 2012/0021224 | A1 | 1/2012 | Everett et al. |
| 2012/0282419 | A1* | 11/2012 | Ahn ........................ B82Y 30/00 428/34.8 |
| 2013/0015409 | A1 | 1/2013 | Fugetsu |
| 2014/0287639 | A1 | 9/2014 | Lee et al. |

FOREIGN PATENT DOCUMENTS

| | | |
|---|---|---|
| CN | 102543464 A | 7/2012 |
| CN | 102674315 A | 9/2012 |
| CN | 103011150 A | 4/2013 |
| CN | 103265013 A | 8/2013 |
| CN | 103310905 A | 9/2013 |
| CN | 103633333 A | 3/2014 |
| EP | 2826836 A1 | 1/2015 |
| JP | 2003-231098 A | 8/2003 |
| JP | 2013-237736 A | 11/2013 |
| JP | 2014-009104 A | 1/2014 |
| KR | 2013-0105345 A | 9/2013 |
| WO | WO-2013/040636 A1 | 3/2013 |
| WO | WO-2013/180661 A1 | 12/2013 |

OTHER PUBLICATIONS

Dreyer et al., "The chemistry of graphene oxide", Chemical Society Reviews, Jan. 1, 2010, vol. 39, pp. 228-240.
Fernandez-Merino et al., "Vitamin C Is an Ideal Substitute for Hydrazine in the Reduction of Graphene Oxide Suspensions", The Journal of Physical Chemistry C, Mar. 4, 2010, vol. 114, No. 14, pp. 6426-6432.
Hung et al., "Cross-linking with Diamine monomers to Prepare Composite Graphene Oxide-Framework Membranes with Varying d-Spacing," Chemistry of Materials, Apr. 14, 2014, vol. 26, No. 9, pp. 2983-2990.
International Search Report and Written Opinion dated Aug. 7, 2015, in International Application PCT/GB2015/050900, 25 pages.
Li et al., "Bio-Inspired Nacre-like Composite Films Based on Graphene with Superior Mechanical, Electrical, and Biocompatible Properties," Advanced Materials, Jul. 3, 2012, vol. 24, Issue 25, 3426-3431.
Lin et al., "Excellent optoelectrical properties of graphene oxide thin films deposited on a flexible substrate by Langmuir-Blodgett assembly", Journal of Materials Chemistry C, Sep. 9, 2013, vol. 1, No. 41, pp. 6869-6877.
Liu et al., "In situ synthesis of the reduced graphene oxide-polyethyleneimine composite and its gas barrier properties", Journal of Materials Chemistry A, Jan. 24, 2013, vol. 1, No. 11, pp. 3739-3746.
Moon et al., "Reduced graphene oxide by chemical graphitization", Nature Communications, Sep. 21, 2010, vol. 1, Article 73, 6 pages.
Park et al., "Graphene Oxide Sheets Chemically Cross-Linked by Polyallylamine," The Journal of Physical Chemistry C: Letters, Aug. 18, 2009, vol. 113, No. 36, pp. 15801-15804.
Pei et al., "Direct reduction of graphene oxide films into highly conductive and flexible graphene films by hydrohalic acids", Carbon, vol. 48, 4466-4474, (2010).
Singapore Written Opinion dated Aug. 28, 2017, in the Singapore Application: 11201607639S, 8 pages.
Su et al., "Impermeable barrier films and protective coatings based on reduced graphene oxide", Nature Communications, Sep. 11, 2014, vol. 5, Article 4843, 5 pages.
Tian et al., "Realizing Ultrahigh Modulus and High Strength of Macroscopic Graphene Oxide Papers Through Crosslinking of Mussel-Inspired Polymers," Advanced Materials, Jun. 4, 2013, vol. 25, Issue 21, pp. 2980-2983.
United Kingdom Search Report dated Oct. 6, 2014, in the United Kingdom application: GB1405642.8, 5 pages.
Yoo et al., "Graphene and graphene oxide and their uses in barrier polymers", Journal of Applied Polymer Science, Jan. 5, 2014, vol. 131, Issue 1, 23 pages.
Zhang et al., "Reduction of graphene oxide via L-ascorbic acid", Chemical Communications (Camb), Feb. 21, 2010, vol. 46, No. 7, pp. 1112-1114.
Zhao et al., "Alternate multilayer films of poly(vinyl alcohol) and exfoliated graphene oxide fabricated via a facial layer-by-layer assembly", Macromolecules, Oct. 28, 2010, vol. 43, No. 22, pp. 9411-9416.
Compton et al., "Graphene Oxide, Highly Reduced Graphene Oxide, and Graphene: Versatile Building Blocks for Carbon-Based Materials," Small, vol. 6, No. 6, pp. 711-723, published online Mar. 11, 2010.
Erickson et al., "Determination of the Local Chemical Structure of Graphene Oxide and Reduced Graphene Oxide," Advanced Materials, vol. 22, 4467-4472, published online Aug. 17, 2010.

* cited by examiner

REDUCED GRAPHENE OXIDE BARRIER MATERIALS

REFERENCE TO RELATED APPLICATIONS

This Application is a U.S. national Stage Entry of PCT International Application No. PCT/GB2015/050900 filed Mar. 26, 2015, which claims priority to GB1405642.8, filed Mar. 28, 2014 and GB1407851.3 filed May 2, 2014, the contents of which are incorporated herein by reference in their entirety.

This invention relates to barrier materials comprising reduced graphene oxide, methods of making said materials and their uses. The reduced graphene oxide is preferably formed from the reduction of graphene oxide by HI, HBr or ascorbic acid.

BACKGROUND

Membranes made from graphene and its chemical derivates show exceptional permeation properties. Defect-free single layer graphene is completely impermeable to all gases and liquids. Due to this intriguing property, graphene-based coating is believed to be a perfect candidate for barrier and protection coating applications. In addition, graphene's mechanical strength, optical transparency, low toxicity and high chemical and thermal stability provide an edge over other barrier materials. However practical applications of graphene based coatings are limited due to the difficulty in growing defect-free large area graphene. It is found that oxidation barrier properties of chemical vapour deposition (CVD) grown graphene with polycrystalline boundaries are actually worse than providing no barrier due to the electrochemical activity of water and oxygen permeated through the defect and grain boundary over an extended period of time. Permeation properties are extremely sensitive to the presence of structural defects and cracks present in the specimens. One possible solution to this problem is to use graphene based multi-layer films.

Difficulty in growing defect free CVD graphene limits the use of CVD graphene for barrier applications. On the other hand despite many efforts to improve the barrier properties of graphene and GO polymer composites, gas permeability is still too high to be used for practical applications.

Graphene oxide (GO) is a chemical derivative of graphene and can be easily and cheaply produced via solution based techniques and can also be easily applied to polymer or other substrates. In dry state it is completely impermeable to all gases and liquids but when exposed to humid condition it acts as a molecular sieve. Even though this property is useful for many applications, its use as a barrier material is limited due to the barrier free water vapour transport. Many practical applications require extremely low water vapour permeation rate $<10^{-6}$ g/m$^2$/day at 100% relative humidity and at room temperature. One of the possible strategies to overcome this issue is to reduce GO and in doing so decrease its water affinity (see Yoo et al; Graphene and graphene oxide and their uses in barrier polymers; *J. Appl. Polym. Sci.;* 2014).

Recently efforts have been made to use multilayers of thermally reduced graphene oxide (rGO), and graphene based composites for the use in ultra-barriers for organic electronics, oxidation resistance coating and anti-corrosion coatings. However the thermally reduced graphene oxide membranes (such as those described in CN102040217 and CN 103633333) are extremely fragile and contain many structural defects leading to finite water permeation rate through these films.

Chemical methods have been used to reduce GO. For example, HI and ascorbic acid reduction have been shown to produce reduced graphene oxide that has a lower oxygen content compared to other reducing methods (Pei, S., Zhao, J., Du, J., Ren, W. & Cheng, H.-M. Direct reduction of graphene oxide films into highly conductive and flexible graphene films by hydrohalic acids. *Carbon* 48, 4466-4474, (2010); Zhang, J. et al. Reduction of graphene oxide via L-ascorbic acid. *Chem Commun (Camb)* 46, 1112-1114, (2010); Moon, I. K., Lee, J., Ruoff, R. S. & Lee, H. Reduced graphene oxide by chemical graphitization. *Nature communications* 1, 73, (2010); Fernández-Merino, M. J. et al. Vitamin C Is an Ideal Substitute for Hydrazine in the Reduction of Graphene Oxide Suspensions. *The Journal of Physical Chemistry C* 114, 6426-6432, (2010)). One problem with chemical reduction techniques is that these also result in structural defects in the rGO. Prior to the present work it was generally accepted that all reduction methods lead to rGO in which the sp$^2$ structure is not restored completely, i.e. rGO with defects in the carbon skeleton still being present (see Yoo et al; Graphene and graphene oxide and their uses in barrier polymers; *J. Appl. Polym. Sci.;* 2014). The existence of defects in chemically reduced GO is a significant hindrance to the use of this material as an effective barrier material and their origin is not properly understood.

CN101812194 describes barrier materials formed from rGO dispersed substantially homogeneously in a polymer matrix.

It is an aim of certain embodiments of this invention to provide a reduced graphene oxide membrane or composite which is substantially impermeable to gases and water, i.e. which exhibits ultralow permeabilities. It is an aim of certain embodiments to provide a rGO membrane which is less permeable than prior art membranes or composites.

Another aim of certain embodiments of the invention is to provide a substantially impermeable reduced graphene oxide membrane or composite which is less fragile and/or chemically stable than prior art membranes or composites.

An aim of certain embodiments of the present invention is to provide an impermeable reduced graphene oxide membrane or composite which exhibits better adhesion with certain substrates (e.g. metals) than prior art membranes or composites.

It is also an aim of certain embodiments of the invention to provide a substantially impermeable reduced graphene oxide membrane or composite which is flexible. A further aim of certain embodiments of the invention is to provide a convenient and/or economical means for forming a barrier material. It is intended that the barrier can be formed in a relatively simple way. Ideally, it is intended that the barrier can be formed in situ.

BRIEF SUMMARY OF THE DISCLOSURE

In accordance with the present invention there is provided the use of a reduced graphene oxide laminate membrane as a barrier material, wherein the reduced graphene oxide is formed from the reduction of graphene oxide with a reducing agent which does not generate a gas (e.g. $CO_2$ or CO) when it reduces graphene oxide.

Thus the present invention provides the use of a reduced graphene oxide laminate membrane as a barrier material, wherein the reduced graphene oxide is formed from the reduction of graphene oxide with a reducing agent which does not generate $CO_2$ or CO as a major component when it reduces graphene oxide and/or wherein reduction of the graphene oxide with the reducing agent leads to the oxygen originating from the graphene oxide which is displaced being substantially or exclusively expelled as water. The reducing agent may be a single reducing agent or it may be a combination of two, three or more different reducing agents. The reducing agent is generally in liquid form. In certain embodiments, the reducing agent is provided in aqueous media. This is most convenient in terms of application and is most environmentally friendly in terms of not giving rise to unwanted effluent. However, mixed liquid media such as aqueous/alcoholic solvent mixtures may also be employed.

In the case of membranes made according to the present invention, reduction of the graphene oxide leads to the oxygen originating from the graphene oxide being expelled as water. In certain embodiments, all of the oxygen which is derived from the GO during the reduction step is expelled as water. In other embodiments, it is possible that a minor proportion, such as up to 35% of the oxygen content derived from reduction of the graphene oxide may also be expelled as $CO_2$ or CO. It is preferable that this proportion is kept as low as possible and should be less than 25%, preferably less than 10% or 5%. In the context of the present invention, the term "substantially" used in relation to the expulsion of water from graphene oxide means that at least 65% of the oxygen originating from the graphene oxide is expelled in the form of water. This does not mean that at least 65% of the oxygen in graphene oxide is removed in the reduction process but that of the amount of oxygen that is removed in the reduction process, at least 65% of this amount. Is expelled as water. Reducing agents which result only in the expulsion of water and which do not result in the expulsion of $CO_2$ or CO, give the best results in the present invention. The skilled person can easily determine by simple chemical experiment which reducing agents produce water as major component or exclusive component and thus which are most appropriate for the present invention. As an illustrative example, gas release can be easily monitored by looking the bubble release during the reduction process.

The term 'as a major component' is intended to mean that of the amount of oxygen that is removed in the reduction process, no more than 15% of this amount is expelled as $CO_2$ or CO. It may be that no more than 10% of the oxygen that is removed in the reduction process is expelled as $CO_2$ or CO. It may be that no more than 5% of the oxygen that is removed in the reduction process is expelled as $CO_2$ or CO. It may be that no more than 2% of the oxygen that is removed in the reduction process is expelled as $CO_2$ or CO.

The reduced graphene oxide membranes of the invention are substantially impermeable and it is intended that they are able to limit any material flux through the reduced graphene oxide layer to a very low level. These materials are therefore considered to be ultra-low permeability membranes.

The reduction will typically not be complete in the sense of reducing graphene oxide completely to graphene. Where the graphene oxide is not completely reduced the resulting material can be considered as either partially oxidised graphene or partially reduced graphene oxide. In certain embodiments of the invention, the degree of reduction of the graphene oxide may result in from 10% to 90% of the original oxygen content of the graphene oxide being removed. More usually, this will be in the region of 40% to 80% of the original oxygen content being removed on reduction. Ideally the amount of reduction is such that about 50% to 60% of the original oxygen content in the graphene oxide is removed, most preferably exclusively in the form of water. In some cases, it is possible to envisage a situation in which reduction leads to complete removal of all of the original oxygen present on graphene oxide; typically, however, total reduction leads to the presence of defects. For this reason, partial reduction is greatly preferred. Having said that, the r graphene oxide may be completely reduced, i.e. the degree of reduction of the graphene oxide may result in from 90% to 100% of the original oxygen content of the graphene oxide being removed.

The partially reduced graphene oxide that is used to form a barrier in accordance with the present invention may, in some cases, contain traces of the reducing agent associated with the graphene matrix. For example, in the case in which HI is used as the reducing agent, it may be possible to identify iodine in the rGO product. It is possible, though not inevitable, that traces of other reducing agents may also remain in the rGO product. Whether or not this is the case depends on the individual reducing agent employed in the reaction.

Although the product can be considered as partially oxidised graphene, we have found that the use of electrochemical graphene as a starting material in a partial oxidation process leads to a partially oxidised product containing substantial defects. This material is not suitable for use as an impermeable barrier.

Preferably, the reducing agent is selected from one or more of: HI, HBr and ascorbic acid (vitamin C). It may be that the reducing agent is HI.

Many reducing agents cause C—C bond breaking upon reduction of graphene oxide, resulting in the release of $CO_2$ and/or CO. Without wishing to be bound by theory it is believed that the release of these gases cause the formation of defects in the carbon skeleton and gaps in the laminar structure. These defects mean that the $sp^2$ structure is not perfectly restored. In the case of reducing agents such as HI, HBr and ascorbic acid, the oxygen is lost from the graphene oxide primarily as water. Thus, the reducing agent may be one which causes the release of oxygen from graphene oxide substantially in the form of water. In principle, any reducing agent that is capable of satisfying this criterion will be effective in the process for preparing barriers according to the present invention.

It is important, however, that any such reducing agent does not otherwise disturb the $sp^2$ structure or lead to an excessive number of defects. Retention of the laminar structure using a reducing agent which does not result in the release of a gas (e.g. $CO_2$ and/or CO from the breaking of C—C bonds in the graphene oxide carbon backbone), but which instead releases water, is important in retaining the laminar structure that leads to the permeability observed.

There is also provided the use of a reduced graphene oxide membrane in a barrier material, the reduced graphene oxide comprising iodine in an amount from 0.01 to 5 atomic % and more preferably in an amount from 0.1 to 5 atomic %.

The reduced graphene oxide laminate may itself be the barrier material but more typically the reduced graphene oxide will be supported on a substrate, e.g. a polymer substrate to form a composite material which acts as the barrier. The rGO laminate may be encapsulated between two substrates, e.g. two polymer substrates. Such encapsulated laminate membranes would be expected to show improved resistance to damage when handled. Such membranes have been shown to have similar permeability properties to free-standing rGO laminates.

An adhesion promoter may be situated between the reduced graphene oxide laminate and the substrate. An 'adhesion promoter' is any substance which increases the strength of the associations between the rGO laminate and/or the graphene oxide laminate precursor and the substrate. The identity of the adhesion promoter will depend on the substrate. Exemplary adhesion promoters for metal substrates include phytic acid, poly(methyl methacrylate) (PMMA) and polystyrene. Exemplary adhesion promoters for glass and silicon based substrates include sodium metasilicate.

The use may be in packaging for perishable products, e.g. foodstuffs, cosmetics, pharmaceutical products. Alternatively it may be in protecting in electronic devices (e.g. as organic light emitting diodes or in liquid crystal displays). It may be used to protect an object from corrosion or from other chemical damage.

The reduced graphene oxide membranes are substantially impermeable to gases and liquids. The membranes are highly stable in aggressive environments and they are inert. They are also mechanically robust and flexible, indeed the membranes have been shown to retain their barrier properties even after repeated folding.

The reduced graphene oxide membranes of the invention may also comprise a cross-linking agent. The cross-linking agent will typically be interspersed throughout the reduced graphene oxide laminate.

A cross linking agent is a substance which bonds with rGO and/or GO flakes. The cross linking agent may form hydrogen bonds with rGO and/or GO flakes or it may form covalent bonds with rGO and/or GO flakes. Examples include diamines (e.g. ethyl diamine, propyl diamine, phenylene diamine), polyallylamines and imidazole. Without wishing to be bound by theory, it is believed that these are examples of crosslinking agents which form hydrogen bonds with rGO and/or GO flakes. Other examples include borate ions and polyetherimides formed from capping the GO with polydopamine. Examples of appropriate cross linking systems can be found in Tian et al, (*Adv. Mater.* 2013, 25, 2980-2983), An et al (*Adv. Mater.* 2011, 23, 3842-3846), Hung et al (Cross-linking with Diamine monomers to Prepare Composite Graphene Oxide-Framework Membranes with Varying d-Spacing; *Chemistry of Materials*, 2014) and Park et al (Graphene Oxide Sheets Chemically Cross-Linked by polyallylamine; J. Phys. Chem. C; 2009)

The cross-linking agent may be a polymer. The polymer may be interspersed throughout the membrane. It may occupying the spaces between reduced graphene oxide flakes, thus providing interlayer crosslinking. Any polymer which does not significantly affect the laminar structure of the rGO would be suitable. The polymer may be PVA (see for example Li et al *Adv. Mater.* 2012, 24, 3426-3431). It has been found that rGO/polymer composite membranes of the type envisaged by the invention exhibit improved adhesiveness to certain substrates (e.g. metals) than rGO membranes which do not comprise a polymer. The amount of polymer in such membranes can be varied from a single molecular layer of polymer to polymer which is multiple molecular layers thick. Other polymers which could be used in this manner include poly(4-styrenesulfonate), Nafion, carboxymethyl cellulose, Chitosan, polyvinyl pyrrolidone, polyaniline, polyallylamines, poly(2-acrylamido-2-methyl-1-propanesulfonic acid), etc. The polymer may comprise a mixture of two or more of the above mentioned polymers. It may be that the polymer is water soluble.

Where the rGO laminate membranes comprise a cross-linking agent (e.g. a polymer or more specifically, PVA), the amount of rGO in the laminate may be from 30 weight % to 98 weight %. The amount of rGO in the laminate membrane may be from 50 weight % to 90 weight %. The amount of rGO in the laminate membrane may be from 60 weight % to 80 weight %.

The reduced graphene oxide membranes of the invention may also comprise a cross linking agent, e.g. a diamine, imidazole, borate ions, polyallylamines, polyetherimide, sodium metasilicate, phytic acid. Sodium metasilicate is particularly well suited to membranes supported on glass or silicon based substrates. Phytic acid is particularly well suited to membranes supported on metal substrates.

The invention also provides a method of making a barrier material, the method comprising the step of reducing graphene oxide to form reduced graphene oxide, with a reducing agent which does not generate a gas (e.g. $CO_2$ or CO) as a major component when it reduces graphene oxide. Optionally, the reducing agent is selected from HI, HBr and ascorbic acid. A particularly suitable reducing agent is HI. As stated above in relation to the use of rGO is a barrier material, in certain embodiments, all of the oxygen which is derived from the GO during the reduction step is expelled as water. In other embodiments, it is possible that a minor proportion, such as up to 35% of the oxygen content derived from reduction of the graphene oxide may also be expelled as $CO_2$ or CO. Thus, the term "major component" used with reference to the generation of $CO_2$ or CO means that these components are produced in an amount corresponding to up to 35% of the oxygen content of the original graphene oxide. Ideally the amount is much lower and, most preferably, all of the oxygen which is derived from the graphene oxide during reduction is expelled as water. As stated above this is not necessarily all of the oxygen content of the graphene oxide itself since in most cases the reduction is a partial reduction of graphene oxide.

Typically, the barrier material will comprise reduced graphene oxide supported on a substrate. The preferred method comprises the following steps:

a) supporting a graphene oxide laminate membrane on a substrate; and
b) reducing the graphene oxide to form a reduced graphene oxide laminate membrane supported on the substrate.

Formation of the graphene oxide membrane and then reducing the graphene oxide in situ allows the formation of a reduced graphene oxide membrane with a substantially perfect laminate structure. The graphene oxide membrane forms a laminate structure in which the layers are held together by hydrogen-bonding. Such good laminate structures would not be obtained if graphene or reduced graphene oxide flakes were formed into a laminate as there are substantially fewer groups on those materials which are capable of hydrogen bonding. Surprisingly, when the graphene oxide membrane is reduced to form the reduced graphene oxide membrane it retains the laminate structure of the graphene oxide membrane, meaning that even better permeability properties are obtained.

In one possible construction of a barrier according to the invention polymer can be intercalated within two adjacent layers (one on either side) of GO and reduction then performed in situ. The water passes through the polymer layer and escapes. This process is most effective when the polymer is a hydrophilic polymer. This type of in situ reduction can be carried out for any GO material deposited on a substrate and, in its simplest form, one possible construction is a layer of GO and a layer of polymer or other material acting as the substrate. In other constructions, there may be several separate GO layers which are spaced apart by one or more substrate layers (each of which may be the same or different). It is important that the or each substrate material is compatible with the reducing agent when in situ reduction is being carried out and the skilled person will be aware of which materials are compatible with the chosen reductant(s).

It may be that step a) involves supporting a graphene oxide polymer composite laminate membrane on a substrate. In this case the step b) will be involve reducing the graphene oxide to form a reduced graphene oxide polymer composite laminate membrane supported on the substrate. Step a) may comprise the steps of i) mixing a suspension of GO with a solution or suspension of a polymer to form a GO/polymer mixture; and ii) depositing the mixture onto the substrate to form a graphene oxide polymer composite laminate membrane supported on a substrate. The GO suspension and polymer solution or suspension are preferably both aqueous. The polymer is preferably PVA. Other polymers which could be used in this manner include poly(4-styrenesulfonate), Nafion, carboxymethyl cellulose, Chitosan, polyvinyl pyrrolidone, polyaniline, polyallylamines, poly(2-acrylamido-2-methyl-1-propanesulfonic acid), etc. The polymer may comprise two or more of the above mentioned polymers. It may be that the polymer is water soluble.

The steps described in the previous paragraph result in GO polymer composite membrane in which the polymer is interspersed throughout the membrane. The polymer may occupy the spaces between reduced graphene oxide flakes, thus providing interlayer crosslinking. Upon reduction the polymer remains in place and a rGO polymer composite membrane results. It has been found that rGO/polymer composite membranes exhibit improved adhesiveness to certain substrates (e.g. metals) when compared to rGO membranes which do not comprise a polymer.

It may be that step a) involves supporting a crosslinked graphene oxide laminate membrane on a substrate. In this case the step b) will be involve reducing the graphene oxide to form a crosslinked reduced graphene oxide laminate membrane supported on the substrate. Step a) may comprise the steps of i) mixing a suspension of GO with a solution or suspension of a crosslinking agent (see above; e.g. a diamine, imidazole, borate ions, polyallylamines) to form a GO/cross-linking agent mixture; and ii) depositing the mixture onto the substrate to form a cross-linked graphene oxide laminate membrane supported on a substrate.

Before the GO membrane is supported on the substrate, the substrate may be modified to increase the strength of the association between the substrate and the GO and/or rGO laminate membrane.

Modifying the substrate may comprise oxidising the surface of the substrate, e.g. by exposing it to ozone and/or oxygen plasma, to form an oxidised polymer substrate. This is an effective way of increasing the association between polymer substrates (e.g. PET) and the GO and/or rGO laminate membrane. Without wishing to be bound by theory, it is believed that the improved adhesion arises from an increase in oxygen functional groups (e.g. hydroxyl, carboxyl, carbonyl etc) on the surface of the substrate. These functional groups may form hydrogen bonds with rGO and/or GO flakes and/or they may form covalent bonds with rGO and/or GO flakes. Modifying the substrate may comprise coating the surface of the substrate with an adhesion promoter. The identity of the adhesion promoter will depend on the substrate. Exemplary adhesion promoters for metal substrates include phytic acid, PMMA and polystyrene. Exemplary adhesion promoters for glass and silicon based substrates include sodium metasilicate.

Irrespective of the construction of the barrier, we have observed that GO can be converted from a super-permeable material before reduction using the chemical reductants according to the process of the present invention into a material which is either substantially or totally impermeable after reduction.

Graphene oxide membranes can be formed by a number of different techniques such as spin coating, spray coating, rod coating and vacuum filtration. For example, the step of forming a graphene oxide membrane on a substrate may comprise applying graphene oxide membrane to the substrate in the form of a paint or an ink. It may comprise spray coating the substrate. The graphene oxide may be applied as a wash. The graphene oxide is then reduced.

Some substrates may be incompatible with the reducing agent. The method may thus comprise the following steps:
a) supporting a graphene oxide membrane on a first substrate;
b) reducing the graphene oxide to form a reduced graphene oxide membrane supported on the first substrate; and
c) transferring the reduced GO membrane from the first substrate to a second substrate.

The desired substrate for supporting the barrier material is the second substrate. The substrate upon which the GO membrane is formed and reduced is a temporary substrate.

Typically, the reducing agent will be applied as a solution, e.g. an aqueous solution. The step of reducing the graphene oxide may comprise applying the reducing agent to the graphene oxide membrane in the form of a paint. Alternatively, it may be sprayed onto the graphene oxide material or it may be applied as a wash. Alternatively, where the reducing agent may take the form of a gas (e.g. HI or HBr), it may be applied as a gas, e.g. by subjecting the graphene oxide membrane to an atmosphere comprising the reducing agent.

In certain embodiments, the barrier material can be provided as a two component coating system. Such a system is analogous to an adhesive system in which an adhesive component and a hardener are provided separately for subsequent combination to provide the adhesive. In the case of the GO barrier, one component of the coating system contains GO flakes provided in a suitable medium and the second component contains the reducing agent (such as HI, HBr, and/or ascorbic acid) which is also provided in a suitable medium.

The graphene oxide membrane may have a thickness from 5 nm to 500 nm.

The step of reducing the graphene oxide may take place at a temperature from about −5° C. to about 150° C., preferably from about 50° C. to about 120° C. and even more preferably from about 70° C. to about 100° C.

The reduction reaction can be followed by eye: graphene oxide is brown and reduced graphene oxide is black and shiny. The graphene oxide membrane may be exposed to the reducing agent until it turns black and shiny. The precise duration of the reduction step for any application will be dependent on a number of factors, in particular the thickness of the membrane. The reduction step may take from about 0.5 minutes to about 120 hours (e.g. from 1 minute to 12 hours), although more usually it will take from about 5 minutes to about 75 minutes. As an example, for HI and HBr, the reduction typically takes from about 0.5 to about 30 minutes (e.g. from about 5 minutes to about 30 minutes) and for ascorbic acid the reduction typically takes from about 30 to about 75 minutes (e.g. from about 45 minutes to about 75 minutes).

The process may further comprise the step of rinsing the reduced graphene oxide membrane with a rinsing agent. The rinsing step may comprise one or more rinses. The precise choice of rinsing agent will depend on the reducing agent used. Typically a polar protic solvent (e.g. water or an organic alcohol with 1, 2 or 3 carbon atoms, e.g. ethanol or methanol) will be used as a rinsing agent. Where HI or HBr is the reducing agent, ethanol may be used as the rinsing agent. Where ascorbic acid is the reducing agent, water may be used as the rinsing agent.

The process may further comprise the step of drying the reduced graphene oxide membrane. This may involve no particular action, i.e. leaving the membrane to dry for a short period or it may involve applying a small amount of heat (e.g. less than about 40° C.) and/or an air stream to the membrane. Thus, after the reduction step, the process may include the deliberate step of drying the rGO membrane. Drying may be achieved by allowing the reduced rGO to stand in, or under reduced pressure, for a period of time from 10 minutes to 6 hours. Alternatively, the temperature may be elevated above ambient temperature for a part of the drying time It may be that the process involves the removal of the substrate from the reduced graphene oxide membrane to provide a free-standing reduced graphene oxide membrane. Preferably, however, the membrane is formed supported on the substrate which, along with the reduced graphene oxide membrane, forms the barrier material.

The invention provides barrier materials prepared using the methods of the invention. The invention also provides a composite barrier material comprising reduced graphene oxide supported on a substrate, the reduced graphene oxide comprising iodine in an amount from 0.1 to 5 atomic %.

The invention also provides packaging for a perishable item (e.g. a foodstuff, a pharmaceutical product, a cosmetic product, a chemical product etc.), the packaging comprising a reduced graphene oxide membrane supported on a polymer substrate, wherein the reduced graphene oxide is formed by the reduction of graphene oxide by a reducing agent selected from HI, HBr and ascorbic acid. The reduced graphene oxide may comprise iodine in an amount from 0.1 to 5 atomic %. Preferably, the reducing agent for use in packaging materials for perishable products is ascorbic acid.

The invention also provides an electronic device comprising a reduced graphene oxide membrane formed by the reduction of graphene oxide by a reducing agent selected from HI and ascorbic acid. The reduced graphene oxide membrane may be supported on substrate, e.g. a polymer substrate. The electronic device may comprise a reduced graphene oxide membrane in which the reduced graphene oxide comprises iodine in an amount from 0.1 to 5 atomic %.

The reduced graphene oxide typically has an oxygen content of from about 5 to about 25 atomic %.

Where HI is the reducing agent, the reduced graphene oxide may comprise iodine in an amount from about 0.1 to about 5 atomic %. The reduced graphene oxide may comprise iodine in an amount from about 0.5 to about 3 atomic % or preferably from about 1 to about 2 atomic %.

Residual amounts of iodine are incorporated into the reduced graphene oxide when HI is used as the reducing agent. Without wishing to be bound by theory, the authors believe that it is possible that this residual iodine contributes to the impermeability of the reduced graphene oxide membranes through interlayer crosslinking.

The substrate may be a polymer substrate, e.g. a polymer film. Examples of polymers which might be suitable include polyethylene (PE), polypropylene (PP), poly(ethylene terephthalate) (PET) and poly(vinyl alcohol) (PVA). The choice of polymer will vary depending on the precise application. PET for example is particularly useful for certain applications (e.g. packaging for perishables). Good adhesion of the rGO membrane to the polymer substrate can be achieved with PVA and this also shows good mechanical properties. Thus, the substrate may be PET film or the substrate may be a PVA film.

The substrate may be silicon based, e.g. an oxidised silicon wafer (which may also support one or more electronic devices or one or more portions of an electronic device).

The substrate may alternatively be metal, e.g. a metal foil or a metal object. Where the substrate is a metal object it could be any size. It could be a small can or similar for the storage of perishable products or, where the membrane is being used to prevent corrosion, it could be a large structure such as a building, bridge or vehicle (e.g. car or boat). In the case of larger structures, the graphene oxide membrane may be applied to the substrate as a paint, and the reducing agent may be applied as a second paint or wash.

The substrate may be flexible, e.g. a flexible polymer substrate.

The substrate may be a porous structure or material. In this case, the method of the invention is a method of reducing the porosity of a porous structure or material. Examples of porous structures and materials include rock (e.g. bedrock), bricks, concrete, buildings, porous polymers.

A particular possible application of the present invention is in the nuclear industry where very low permeability coating can be applied using the methods of the invention to materials or structures used in the nuclear industry. The barrier of the present invention may find other applications in the nuclear industry such as the containment of radioactive waste or spillages. Barriers may thus be used for containers or may be used in the form of geotextile materials that could be used to segregate zones on a nuclear site.

In a further aspect of the invention is provided a reduced graphene oxide laminate membrane in which a polymer is interspersed throughout the membrane, wherein the reduced graphene oxide membrane is affixed to a metal substrate. Preferably, the polymer is PVA. The polymer could also be include poly(4-styrenesulfonate), Nafion, carboxymethyl cellulose, Chitosan, polyvinyl pyrrolidone, polyaniline etc. The reduced graphene oxide laminate membrane will typically have been formed from the reduction of the corresponding graphene oxide laminate with a reducing agent which does not generate $CO_2$ or CO when it reduces graphene oxide and/or wherein reduction of the corresponding graphene oxide laminate with the reducing agent leads to the oxygen originating from the graphene oxide being substantially or exclusively expelled as water, e.g. a reducing agent selected from HI, HBr and ascorbic acid.

In a further aspect of the invention is provided a barrier material comprising:
an oxidised polymer substrate; and
a reduced graphene oxide laminate membrane.

Preferably, the oxidised polymer is oxidised PET. The oxidised polymer substrate may be formed by oxidising the surface of a polymer substrate, e.g. by exposing it to ozone and/or oxygen plasma. The reduced graphene oxide laminate membrane will typically have been formed from the reduction of the corresponding graphene oxide laminate with a reducing agent which does not generate $CO_2$ or CO when it reduces graphene oxide and/or wherein reduction of the corresponding graphene oxide laminate with the reducing agent leads to the oxygen originating from the graphene oxide being substantially or exclusively expelled as water, e.g. a reducing agent selected from HI, HBr and ascorbic acid. The term 'oxidised polymer substrate' is intended to mean that the polymer substrate (and particularly the surface of the polymer substrate) has a higher oxygen content than the polymer usually has. It is not intended to mean simply that the polymer comprises oxygen.

In a further aspect of the invention is provided a reduced graphene oxide laminate membrane, wherein the reduced graphene oxide membrane is affixed to a metal substrate and an adhesion promoter is dispersed throughout the reduced graphene oxide laminate and/or or between the reduced graphene oxide laminate and the substrate. The adhesion promoter may be a polymer, e.g. PMMA, PVA, polystyrene, poly(4-styrenesulfonate), Nafion, carboxymethyl cellulose, Chitosan, polyvinyl pyrrolidone, polyaniline. The adhesion promoter may be phytic acid. The reduced graphene oxide laminate membrane will typically have been formed from the reduction of the corresponding graphene oxide laminate with a reducing agent which does not generate $CO_2$ or CO when it reduces graphene oxide and/or wherein reduction of the corresponding graphene oxide laminate with the reducing agent leads to the oxygen originating from the graphene oxide being substantially or exclusively expelled as water, e.g. a reducing agent selected from HI, HBr and ascorbic acid.

In a further aspect of the invention is provided a reduced graphene oxide laminate membrane, wherein the reduced graphene oxide membrane is affixed to a glass or silicon based substrate and an adhesion promoter is dispersed throughout the reduced graphene oxide laminate and/or or between the reduced graphene oxide laminate and the substrate. The adhesion promoter may be sodium metasilicate. The reduced graphene oxide laminate membrane will typically have been formed from the reduction of the corresponding graphene oxide laminate with a reducing agent which does not generate $CO_2$ or CO when it reduces graphene oxide and/or wherein reduction of the corresponding graphene oxide laminate with the reducing agent leads to the oxygen originating from the graphene oxide being substantially or exclusively expelled as water, e.g. a reducing agent selected from HI, HBr and ascorbic acid.

In any of the above described aspects of the invention the reducing agent may be HI or HBr. The HI or HBr may used as a solution or as a gas. Alternatively they can be formed in situ, e.g. from a mixture of one or more halide salts and one or more acids. Furthermore, the reducing agent may be a combination of HI or HBr and another acid, e.g. acetic acid.

The invention may also be described in any of the numbered paragraphs:

1. The use of a reduced graphene oxide membrane in a barrier material, wherein the reduced graphene oxide is formed from the reduction of graphene oxide with a reducing agent which does not generate $CO_2$ or CO when it reduces graphene oxide and/or wherein reduction of the graphene which is displaced oxide with the reducing agent leads to the oxygen originating from the graphene oxide being substantially or exclusively expelled as water.
2. The use as described in paragraph 1, wherein the reducing agent is a single reducing agent or is a combination of two or three different reducing agents.
3. The use as described in paragraph 1 or 2, wherein the reducing agent is in liquid form.
4. The use as described in any of paragraphs 1, 2 or 3, wherein up to 35% of the oxygen content derived from reduction of the graphene oxide is expelled as $CO_2$ or CO.
5. The use as described in any preceding paragraph, wherein the degree of reduction of the graphene oxide results in from 10% to 90% of the original oxygen content of the graphene oxide being removed.
6. The use as described in any preceding paragraph, wherein the reducing agent is selected from one or more of: HI, HBr and ascorbic acid (vitamin C).
7. The use as described in any preceding paragraph, wherein the reduced graphene oxide is supported on a substrate to form a composite material which acts as a barrier.
8. The use as described in any preceding paragraph, wherein the reduced graphene oxide comprising iodine in an amount from 0.01 to 5 atomic %.
9. The use as described in any preceding paragraph, wherein the reduced graphene oxide membrane further comprises a polymer interspersed through the membrane.
10. The use as described in paragraph 9, wherein the polymer is PVA.
11. A barrier material comprising reduced graphene oxide in accordance with any of paragraphs 1 to 10 supported on a substrate.
12. A method of making a barrier material, the method comprising the step of reducing graphene oxide to form reduced graphene oxide, with a reducing agent which does not generate $CO_2$ or CO as a major component when it reduces graphene oxide.
13. A method of preparing a reduced graphene oxide membrane on a substrate, the method comprising the following steps:
   a) supporting a graphene oxide membrane on a substrate; and
   b) reducing the graphene oxide to form a reduced graphene oxide membrane supported on the substrate.
14. A method of any one of paragraphs 12 to 13, wherein the method is a method of reducing the porosity of a porous material or structure and wherein, where present, the substrate is the porous structure or material.

BRIEF DESCRIPTION OF THE DRAWINGS

Embodiments of the invention are further described hereinafter with reference to the accompanying drawings, in which:

FIG. 8 shows the influence of mechanical deformation on barrier properties. a —He permeation through 40 nm Al and 200 nm HI-rGO (both on 12 μm PET) before and after multiple folding. Inset: photograph of the tested HI-rGO. b—He permeation through bare PET, 40 nm thick Al on PET and <50 nm thick HI-rGO on PET before and after their straining. The strain was created by an argon pressure of 2 bar applied to one side of the membranes with vacuum on the other side.

DETAILED DESCRIPTION

Figure 1:
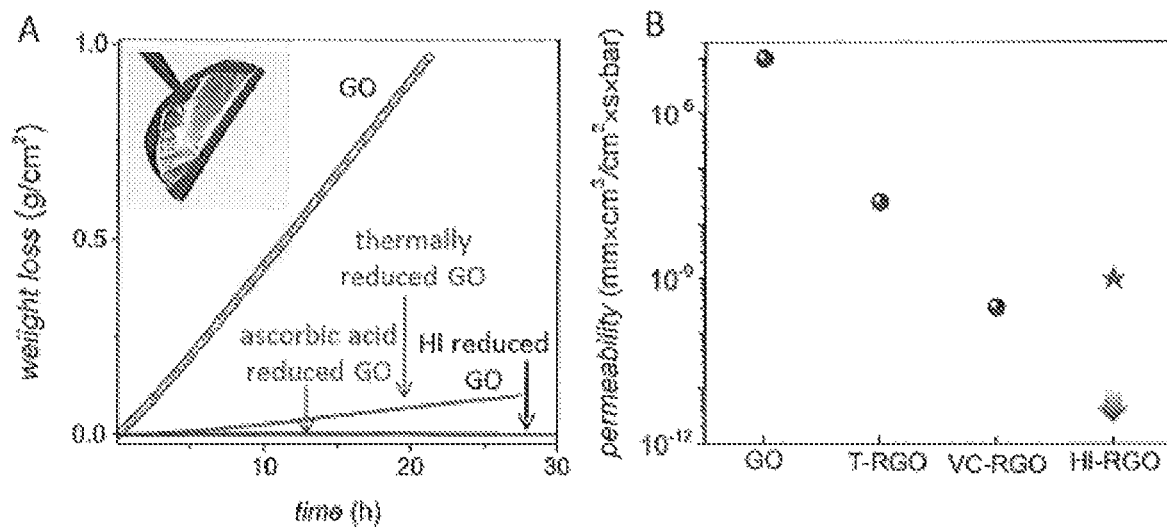
FIG. 1 shows water permeation through GO and rGO membranes. (A) Weight loss of a container enclosing water sealed with GO and different rGO membranes with a thickness of 500 nm. Inset shows optical photographs of a HI acid-reduced GO. (B) Water permeability of GO and GO reduced with different techniques (Arrow indicates the detection limit of our experiment). Star symbol is for water vapour permeability of a 40 nm metalized PET.

A barrier material is a material which is substantially impermeable to gases and water vapour. The exact permeability at which a material becomes a barrier material depends on the specific application. Organic light emitting diodes and other electronic applications often require a material which is more impermeable than might be required in certain food packaging applications. As a rule of thumb, throughout this specification a barrier material is one having a water permeability below $10^{-6}$ g/m²/day at 100% RH and room temperature. However, for certain less critical applications, a water permeability below $10^{-5}$ g/m2/day at 100% RH and room temperature, or even a water permeability below $10^{-4}$ g/m2/day at 100% RH and room temperature, may be acceptable. These materials exhibit a relatively larger degree of transmission of gases and water vapour. in the particular applications concerned, this might be perfectly acceptable. The skilled person will be able to determine the appropriate level of impermeability for any particular application. The degree of permeability is permissible thus depends exactly the purpose that the barrier of the present invention is being used for. For example, in the case of barrier materials that might be used for nuclear applications a very low level of permeability, for example, a water permeability below $10^{-6}$ g/m2/day at 100% RH and room temperature may be more appropriate whereas in food packaging applications for less sensitive foodstuffs a much lower level of impermeability i.e. a higher permeability such as a water permeability below $10^{-4}$ g/m2/day at 100% RH and room temperature Atomic percentage is defined as the number of atoms in element in 100 atoms representative of the substance. Mathematically, the atomic percent is atomic percent $$(i) = \frac{N_i}{N_{tot}} \times 100\%$$

where $N_i$ are the number of atoms of interest and $N_{tot}$ are the total number of atoms. The atomic % therefore can be represented as 100*number of atoms of one component/total number of all atoms in sample, which is the same as 100*number of moles of one component/number of moles of all components.

Reduced graphene oxide is graphene oxide which has been reduced. It is not pristine graphene as it retains some oxygen content. It is substantially less oxygenated than graphene oxide.

The present invention involves the use of reduced graphene oxide membranes which may be formed from graphene oxide membranes. The reduced graphene oxide membranes and graphene oxide membranes are laminate membranes. They comprise stacks of individual graphene oxide flakes, in which the flakes are predominantly monolayer reduced graphene oxide or graphene oxide respectively. Although the flakes are predominantly monolayer reduced graphene oxide or graphene oxide respectively, it is within the scope of this invention that some of the reduced graphene oxide or graphene oxide is present as two- or few-layer reduced graphene oxide or graphene oxide. Thus, it may be that at least 75% by weight of the reduced graphene oxide or graphene oxide is in the form of monolayer reduced graphene oxide or graphene oxide flakes, or it may be that at least 85% by weight of the reduced graphene oxide or graphene oxide is in the form of monolayer reduced graphene oxide or graphene oxide flakes (e.g. at least 95%, for example at least 99% by weight of the reduced graphene oxide or graphene oxide is in the form of monolayer reduced graphene oxide or graphene oxide flakes) with the remainder made up of two- or few-layer reduced graphene oxide or graphene oxide.

The graphene oxide for use in this application can be made by any means known in the art. In a preferred method, graphite oxide can be prepared from graphite flakes (e.g. natural graphite flakes) by treating them with potassium permanganate and sodium nitrate in concentrated sulphuric acid. This method is called Hummers method. Another method is the Brodie method, which involves adding potassium chlorate ($KClO_3$) to a slurry of graphite in fuming nitric acid. For a review see, Dreyer et al. *The chemistry of graphene oxide, Chem. Soc. Rev.,* 2010, 39, 228-240.

Individual graphene oxide (GO) sheets can then be exfoliated by dissolving graphite oxide in water or other polar solvents with the help of ultrasound, and bulk residues can then be removed by centrifugation and optionally a dialysis step to remove additional salts. Thus, exfoliation of graphite oxide in water into individual graphene oxide can be achieved by the sonication technique followed by centrifugation at 10000 rpm to remove few layers and thick flakes. Graphene oxide membranes can be formed by restacking of these single layer graphene oxides by a number of different techniques such as spin coating, spray coating, rod coating and vacuum filtration.

Graphene oxide was prepared by Hummers method and that was dispersed in water by sonication to make stable dispersions of graphene oxide in water. We used mainly two types of samples, free standing membranes and GO or rGO coated substrates such as 12 µm PET, 25-100 µm metal foils and 290 nm oxidised silicon wafers for our experiments. For fabricating free standing membranes, GO dispersions were vacuum filtered to obtain free standing GO membranes with thickness ranging from 500 nm to 5 µm. GO coating on different substrates were fabricated by rod-coating technique. GO membranes and GO coatings were reduced mainly by thermal and chemical routes. Thermal reduction was carried out at 300° C. for four hours in 10% hydrogen argon gas mixture and chemical reductions were carried out using previously reported HI acid and ascorbic acid reduction methods (Pei, S., Zhao, J., Du, J., Ren, W. & Cheng, H.-M. Direct reduction of graphene oxide films into highly conductive and flexible graphene films by hydrohalic acids. *Carbon* 48, 4466-4474, (2010); Zhang, J. et al. Reduction of graphene oxide via L-ascorbic acid. *Chem Commun (Camb)* 46, 1112-1114, (2010); Moon, I. K., Lee, J., Ruoff, R. S. & Lee, H. Reduced graphene oxide by chemical graphitization. *Nature communications* 1, 73, (2010); Fernández-Merino, M. J. et al. Vitamin C Is an Ideal Substitute for Hydrazine in the Reduction of Graphene Oxide Suspensions. *The Journal of Physical Chemistry C* 114, 6426-6432, (2010)).

HI reductions were carried out by exposing GO membranes or GO coatings to HI acid vapours at 90° C. for several minutes. The reduction time were varied from 0.5-30 minutes depending on the thickness of the membranes or coatings, this is to achieve the complete reduction of GO. After the reduction, the samples were rinsed with ethanol for several times to remove the residual HI acid and finally the samples were dried in air. For ascorbic acid reduction, the GO membranes or GO coatings were immersed into the ascorbic acid solution with a concentration of 30 mg/ml for 1 hour at 90° C. The samples were further rinsed with water and finally dried in air. Permeation properties of GO and rGO samples were measured. In brief, for vapour permeation, free standing membranes and rGO coated PET were glued to a Cu foil with an opening of 1 cm in diameter and placed between two O-rings of a specially designed metal container. Vapour permeability was measured by monitoring the weight loss of the container filled with solvents or water with time by using a computer controlled precision balance (Denver instruments). For gas permeation measurements, we used standard vacuum components incorporated with the vacuum flanges to allow pumping, pressure gauges and controlled supply of gases. rGO coated PET were placed between two rubber gaskets and pressurised (up to 1 Bar) from one side and monitored the gas leak on the other side by using mass spectrometry. We used helium-leak detector INFICON UL200 which allowed detection of helium and hydrogen.

FIG. 1A shows an example of the water vapour permeation through GO and rGO free-standing membranes with a thickness of 0.5 µm. In agreement with our previous reports free standing GO membranes are completely impermeable to all gases but shows unimpeded water vapour permeation. The same sample after annealing at 300° C. shows ten times less water vapour permeation but they are extremely fragile. Water vapour permeation of different thermally reduced samples at similar thermal reduction conditions varied widely (by a factor of <60%). Without wishing to be bound by theory, this variation could be explained by the different extent of structural defects present in the sample. In contrast, chemically reduced samples show consistent water permeation rates and are orders of magnitude lower than the thermally reduced GO membranes. HI acid reduced GO exhibits the best barrier property towards water vapour and it was below our detection limit of <0.1 mg for several days, this gives an upper limit on water vapour permeation through HI acid reduced GO membranes as $10^{-11}$ mm·g/cm²·s·bar, two orders of magnitude less than the currently commercially used metallised PET films. FIG. 1B compares the permeability values of GO and GO reduced with thermal and chemical techniques. We have also performed permeation experiments for other organic solvents such as acetone, methanol, ethanol, propanol etc. and found none (for clarity of the plots data is not included in FIG. 1).

Figure 2:
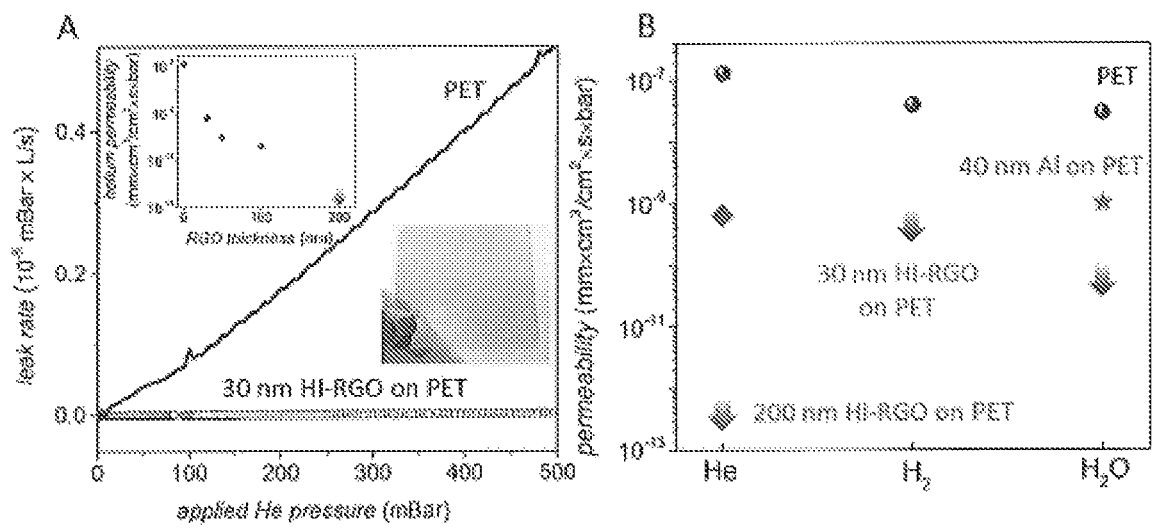
FIG. 2 shows water and gas Permeation through rGO coated PET. (A) Examples of He-leak measurements for a bare 12 μm thick PET and PET coated with a 30 nm thick HI-reduced GO. Upper inset shows the dependence of the He-permeability on rGO thickness. Star symbol is for He permeation through a 50 nm thick ascorbic acid reduced GO coating. Lower inset shows the optical photograph of a 30 nm rGO coated PET with an optical transparency of ~35%. Optical transparency of a 100 nm thick rGO on PET is 7% and 200 nm thick rGO is completely opaque. (B) Comparison of permeability of HI-rGO on PET with respect to bare PET for He, $H_2$ and $H_2O$ (Arrows indicate the detection limit of our experiment). Star symbol is for water vapour permeability of a 40 nm metalized PET.

To evaluate the permeation properties of ultra-thin chemically reduced GO coatings and to assess its application for barrier coating, we have further investigated the gas and vapour permeation properties of thin layers of rGO on PET. FIG. 2 show the permeation properties of thin layers of HI acid reduced GO on a 12 µm PET. Thickness of rGO coating on PET was measured by atomic force microscopy (AFM) and also by measuring the optical transmittance at 550 nm. To evaluate the gas (He and $H_2$) barrier properties of these films we used He-leak detector. He is found to be the best probe gas to study permeation properties of PET or any polymer films because of its small size and high diffusion coefficient over all other gases. Our 12 µm PET show a He permeability of $10^{-7}$ mm·cm³/cm²·s·bar, in agreement with literature values. He permeation through a 30 nm thick rGO coated PET (see FIG. 2A bottom inset) is more than two orders of magnitude lower than that of bare PET. FIG. 2A upper inset shows the thickness dependence of He permeation on rGO thickness and found that 200 nm rGO coating is enough to block the He completely, the permeation rate is at least 5 order of magnitude less than the uncoated PET. Moisture barrier properties of these rGO coated PET were measured by gravimetric techniques and found that 30 nm rGO coating is enough to stop water vapour permeation completely. Our experimental detection limit for water vapour permeation is shown in FIG. 2B. In comparison with 40 nm metallised (Al) PET, water permeation through a 30 nm rGO coated PET is at least one order of magnitude smaller. We have also tested ascorbic acid reduced GO on PET and didn't find any considerable variation for He or water vapour permeation rate (See FIG. 2A upper inset). This exceptional permeation property of rGO coated PET opens many possible applications in barrier coating especially in packaging (e.g. food and pharmaceutical packaging). It is also important to note that the adhesion between rGO and PET is strong enough to withstand many cycles of measurements and also mechanical scratching, stretching and folding.

Figure 3:
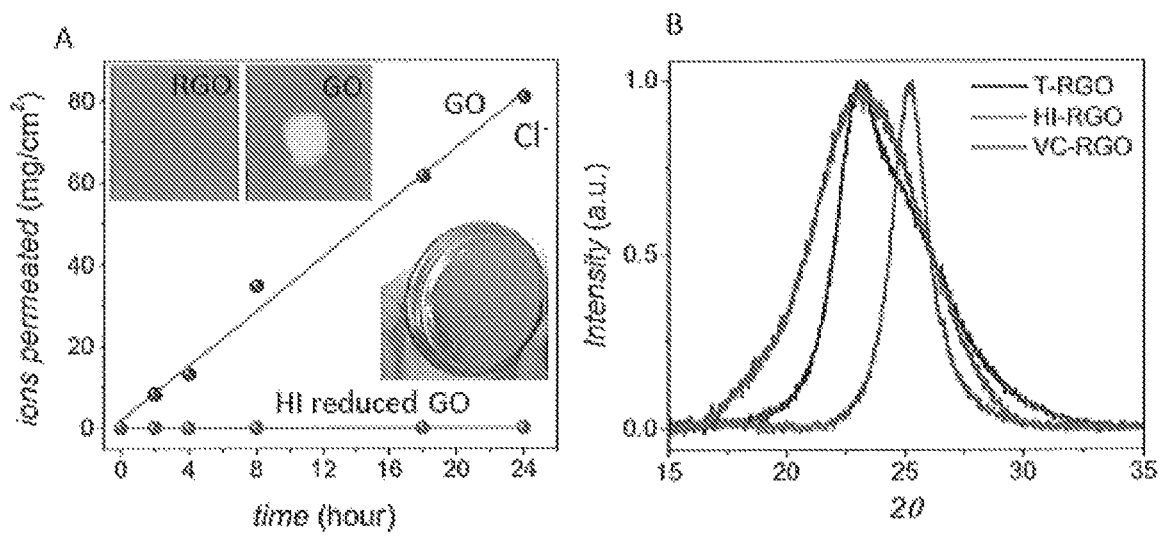
FIG. 3 shows salt barrier properties of HI-rGO. (A) Cl⁻ ion permeation through a 1 μm thick GO membrane from the feed side with 1M NaCl before and after reduction with HI acid. Upper Inset—optical photographs show the effect of HF acid drop testing on a 290 nm oxidised silicon substrate (1 cm×1 cm) coated with a 500 nm thick GO and rGO, after removing the GO/RGO layer. White centre region in the GO coated sample is due to the etching of $SiO_2$ by HF acid. Bottom inset—Photograph of a 1 μm thick HI-RGO coated/lined glass petri dish. (B) X-ray diffraction for thermally reduced, HI acid and ascorbic acid reduced GO membranes.

Superior water and gas barrier behaviours of rGO membranes and coatings lead us to further investigate the salt permeation properties, which could be used in the anticorrosion and chemical resistant coating or lining applications. The salt permeation properties of rGO membranes were measured as follows. Briefly 1M salt solution (NaCl) and water were filled in a U-shaped two-compartment container separated with a rGO membrane. Salt diffusion through the membranes was monitored by measuring the salt permeated to the pure water side by ion chromatography and gravimetric technique. FIG. 3 shows an example of Cl⁻ permeation through a reference GO and HI acid reduced GO membrane with time. As reported previously our GO membranes allow ultrafast permeation of salt while after reduction we didn't detect any permeation of salt through the membrane. Our detection limit for the salt permeation through rGO membrane is at least 1000 times less than through the pristine membranes. We have also measured salt permeation through ascorbic acid reduced GO and found no salt permeation. To explore the salt barrier property of these membranes towards various applications, especially for chemical protection and anticorrosion coatings, we have coated 290 nm Si/SiO$_2$ substrate with GO and RGO and then treated it with hydrofluoric (HF) acid by dropping HF acid on top of the coating for few hours. HF is considered as the most corrosive and toxic acid. FIG. 3 inset shows the optical photographs of the substrates after the drop testing and removal of the protective coating. As evident from the figure, HF permeated through a 500 nm thick GO and etched the 290 nm SiO$_2$ layer completely while the same thickness RGO completely blocked the permeation of HF. Further we have also carried out drop testing for ascorbic acid-rGO coated metal foils (e.g. Cu and Ni) to nitric and sulphuric acid solutions with different concentrations (from 0.05 M to highly concentrated) and found no degradation or etching of metal foils for at least 48 hours. We have also immersed ascorbic acid-rGO coated Ni and steel plate to saturated iron chloride and sodium chloride solution for few days and found no degradation for Ni and steel plates. These simple experiments show the potential of high quality reduced GO for chemical protection and anticorrosion coatings or linings. FIG. 3A bottom inset shows an example of rGO lining. We have successfully coated a glass Petri dish with 1 μm GO by using spray coating and reduced it with HI acid. The rGO lined Petri dish shows good chemical resistance to HF acid for many days. PVA/rGO membranes such as those described in Example 3 below have also been shown to be impermeable to HF.

Without wishing to be bound by theory, we can explain the observed barrier properties of high quality reduced GO using the known mechanisms of reduction process and the structure of reduced GO. Molecular and ionic permeation in GO membranes mainly occurs through the interlayer capillary between GO sheets and the capillary width for pristine graphene oxide varies from 0.7 nm to 1.3 nm depending on the humidity or water content. After the chemical or thermal reduction this interlayer capillary collapses and the interlayer distance reduces to 0.36±0.01 nm (see FIG. 3B). This reduced interlayer spacing is not adequate for water or any other gases to permeate through the membranes. The quality of reduction can be easily judged form the X-ray diffraction peak for different rGO samples. FIG. 3B shows the diffraction peak for GO membranes reduced with thermal, VC and HI acid. The sharper x-ray peak of HI acid-reduced samples compared to other two shows higher degree of graphitization. Even though the degree of graphitization is slightly lower (Broader X-ray peak) in ascorbic acid-rGO, it shows nearly the same permeation properties as that of HI-rGO membranes or coatings. The only difference we found between HI acid and ascorbic acid reduced GO is the water vapour permeation through free standing rGO membranes. Water permeation through ascorbic acid-rGO is one order of magnitude higher than the HI-rGO membranes. On the other hand ultra-thin layers ascorbic acid and HI acid reduced GO coating on PET shows similar properties. This could be due to the difficulty in the complete reduction of 500 nm thick membrane with ascorbic acid compared to thin coatings. The observed remarkable difference in permeation properties of ascorbic acid reduced GO and thermally reduced GO indicates that other than the degree of graphitization, the amount of atomic defects formed during the reduction process may be crucial for the permeation properties. During the thermal reduction, oxygen containing functional groups decomposes and releases as CO and CO$_2$ gases. The decomposition of oxygen containing functional groups may also remove carbon atom from the graphene plane and result in distortion in graphene lattice. On the other hand during the chemical reduction with ascorbic acid and HI acid, it is believed that the oxygen containing functional groups chemically react with the reducing agents and mainly releases oxygen as water molecule instead of carbon containing gases. It may be that this results in less structural disorder and higher graphitization of chemically reduced GO. This can be seen from the very shiny and smooth surface of high quality reduced GO.

In conclusion, high quality HI acid reduced GO membranes show perfect barrier properties towards different gases, salts and water vapours. These properties of high quality rGO can be useful in different practical applications such as 02 and moisture barrier coating for electronics, food and pharmaceutical packaging and chemical and corrosion protection applications. The scalability and solution processability of this technique is highly advantages for various applications. Even though HI acid reduced GO shows the perfect barrier property, we envisage that it might not be suitable for all applications. However the ascorbic acid reduced GO also shows nearly the same barrier properties as that of HI acid reduced GO and may be suitable for applications in which the HI reduced GO would not be suitable.

EXAMPLE 1

Optical and AFM Characterisation of HI-rGO on PET

Figure 4:
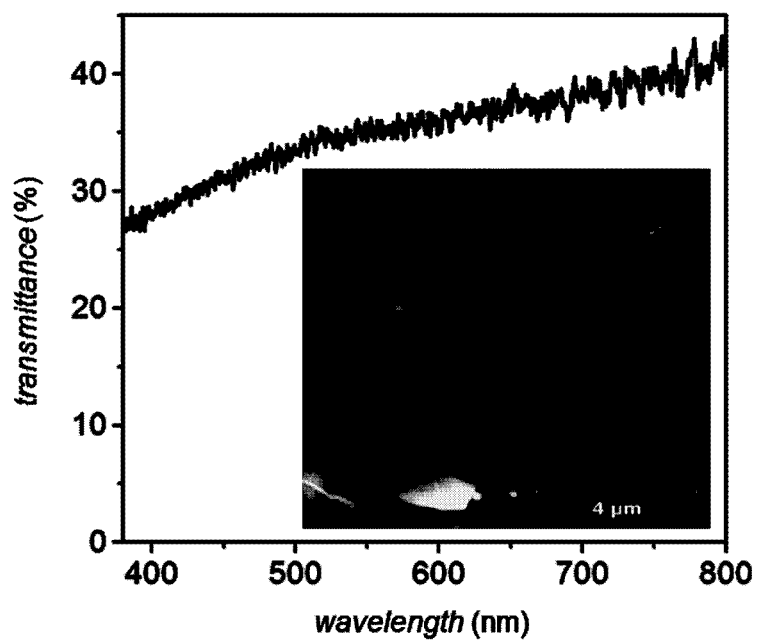
FIG. 4 shows the optical transmittance for a 30 nm thick HI-rGO on top of 12 μm thick PET with respect to bare PET. The inset shows an AFM image of the film near the boundary between bare PET and the rGO coating. Blue curve: Height profile along the gray line.

To characterize rGO films on PET scanning electron microscopy (SEM), atomic force microscopy (AFM) and optical absorption spectroscopy were used. FIG. 4 shows an absorption spectrum for a 30 nm thick film of HI-RGO. For the visible spectrum the transmittance varies from ≈30 to 40%. The thickness of RGO coatings was measured using a Veeco Dimension 3100 AFM in the tapping mode under ambient conditions. The inset of FIG. 4 shows a representative AFM image for a 30 nm thick HI-rGO on PET.

EXAMPLE 2 rGO Coating on Rough and Porous Surfaces

Figure 5:
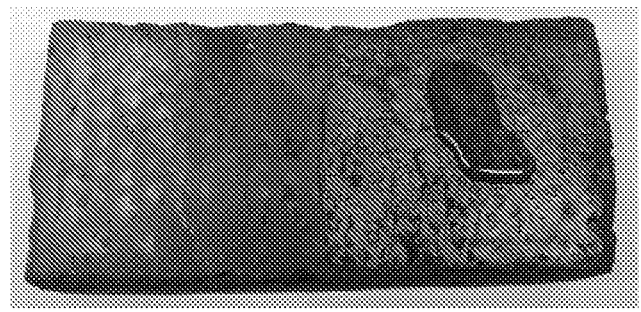
FIG. 5 shows a photograph demonstrating water permeation through a brick (~20 cm long) with and without ascorbic acid-rGO coating. Brick without the graphitic coating rapidly absorbs water but it can stay on top of the ascorbic acid-rGO coated part for many hours.

To understand the effect of surface roughness and porosity on the barrier properties of our rGO films, we have deposited GO onto various surfaces. Those included polymer materials such as porous polycarbonate, polyvinylidene fluoride, polysulfone, etc. and extremely rough substrates such as brick and concrete surfaces. GO laminates on all these substrates were reduced by treating them with an ascorbic acid solution at 80° C. for 2 hours or 50° C. for 24 hours. We have found that, although the barrier quality can be sensitive to roughness and porosity, GO laminates provide a high permeation barrier for all tested surfaces. As an example, FIG. 5 shows a photograph of a conventional red brick that is half coated with ascorbic acid-rGO. If water is poured on the brick, it stays only on the part covered with highly hydrophobic rGO. One can quantify the barrier properties of ascorbic acid-rGO by measuring the time required for disappearance of the water puddle (FIG. 5). The brick without any coating absorbs water within a few seconds. In contrast, water on top of the RGO coated part stays for many hours and eventually disappears mainly because of evaporation. Taking the evaporation into account, we estimate that ascorbic acid-rGO treated bricks are ~4,000 times more water repellant than uncoated bricks.

EXAMPLE 3

Polyvinyl Alcohol Modified GO for Improved Adhesion

Adhesion between treated surfaces and rGO is critical for the perspective use of such films as chemical and anticorrosion coatings. Adhesion of rGO to plastic and glass surfaces has been found strong. Qualitatively, the graphitic films were as robust as the standard barrier films (40 nm Al on PET) but the wear properties require further studies and quantification. In contrast, adhesion of rGO to metal surfaces was weak, which resulted in easy scratching and partial peeling of the protective coating. To overcome the drawbacks of weak adhesion to metal surfaces, we have provided the GO laminates with interlayer cross-linking with PVA. For the purpose of this report, we have tested permeation properties of PVA-GO composite films, both before and after their chemical reduction.

Figure 6:
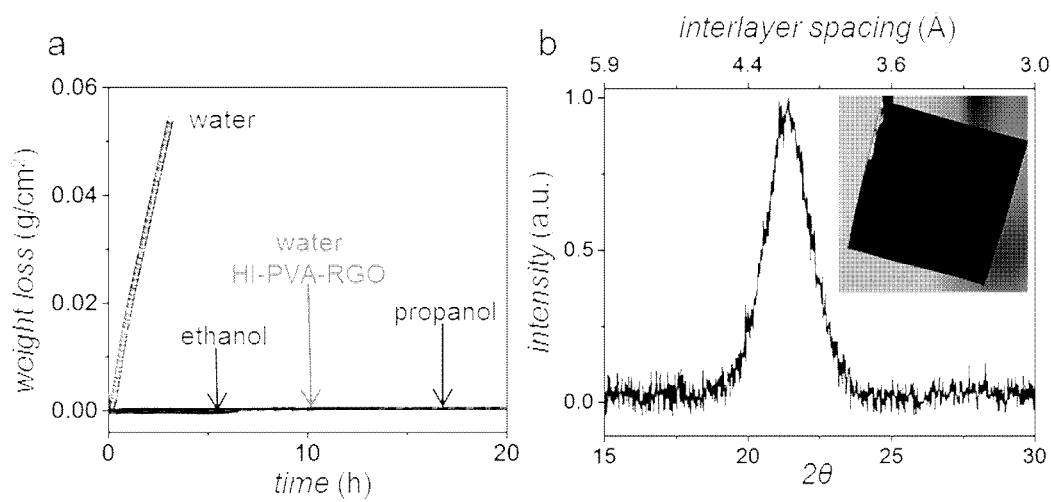
FIG. 6 shows PVA-GO composites films exhibit barrier properties similar to those of GO laminates but with improved mechanical strength. a—Weight loss for a container filled with water or other liquids and sealed with a 1 μm thick PVA-GO membrane before and after its reduction with HI acid. The measurements were carried out at room temperature in a glove box. The green curve shows water permeation after the reduction in HI; the other curves are for non-reduced PVA-GO. b—X-ray diffraction for HI-reduced PVA-GO membrane

PVA-GO samples were prepared by blending water solutions of GO and PVA by using a magnetic stirrer. The concentrations were chosen such that we achieved 60-80 weight percentage of GO in the final laminates, after water evaporated. All the tested PVA-GO films exhibited similar properties, irrespective of their PVA fraction. We used vacuum filtration, drop casting and rod coating techniques to produce free standing PVA-GO membranes and PVA-GO coated substrates. FIG. 6a shows examples of our permeation measurements for water and other organic vapors through a 1 µm thick PVA-GO membrane, before and after its reduction with HI. Similar to GO, PVA-GO membranes completely block all gases and vapors except for water. After reduction of PVA-GO with HI, the water permeation is reduced approximately by four orders of magnitude (FIG. 6).

We have also studied salt permeation properties of such cross-linked GO membranes and found that permeation rates are beyond our detection limit, too. We have tested not only HI- but also ascorbic acid-reduced PVA-GO and observed no major differences. The inset of FIG. 6b shows an optical photograph of a steel plate coated with ascorbic acid reduced PVA-rGO. Such protecting coatings exhibit good adhesion to metal surfaces including copper, steel, nickel, etc. Copper foils coated with ascorbic acid-reduced PVA-GO were tested for acid corrosion. We could not detect any sign of corrosion in tests similar to those described in the main text and involving oxidized Si wafers protected with unmodified rGO (FIG. 3a).

FIG. 6b shows X-ray diffraction for HI-reduced PVA-rGO membranes. They exhibit a layered structure similar to HI-RGO but with an interlayer separation of ≈4.2 Å, that is, considerably larger than in the membranes without PVA (see FIG. 3b). This increase in the interlayer distance is attributed to the presence of PVA molecules between reduced GO sheets (intercalation-like composites). Although the interlayer distance increases, the presence of polymer molecules trapped between the graphene sheets effectively blocks all molecular and ionic permeation through the extra space of 0.6 Å in the composite membranes.

Membranes were also prepared using polyvinylpyrrolidinone and imidazole as cross linkers respectively. The methods carried out were substantially the same as for the PVA crosslinked membranes. In the case of imidazole GO was stirred with imidazole at 80 C to get better cross-linking.

EXAMPLE 4 the Effect of Reduction Conditions on Ascorbic Acid Reduced GO

Figure 7:
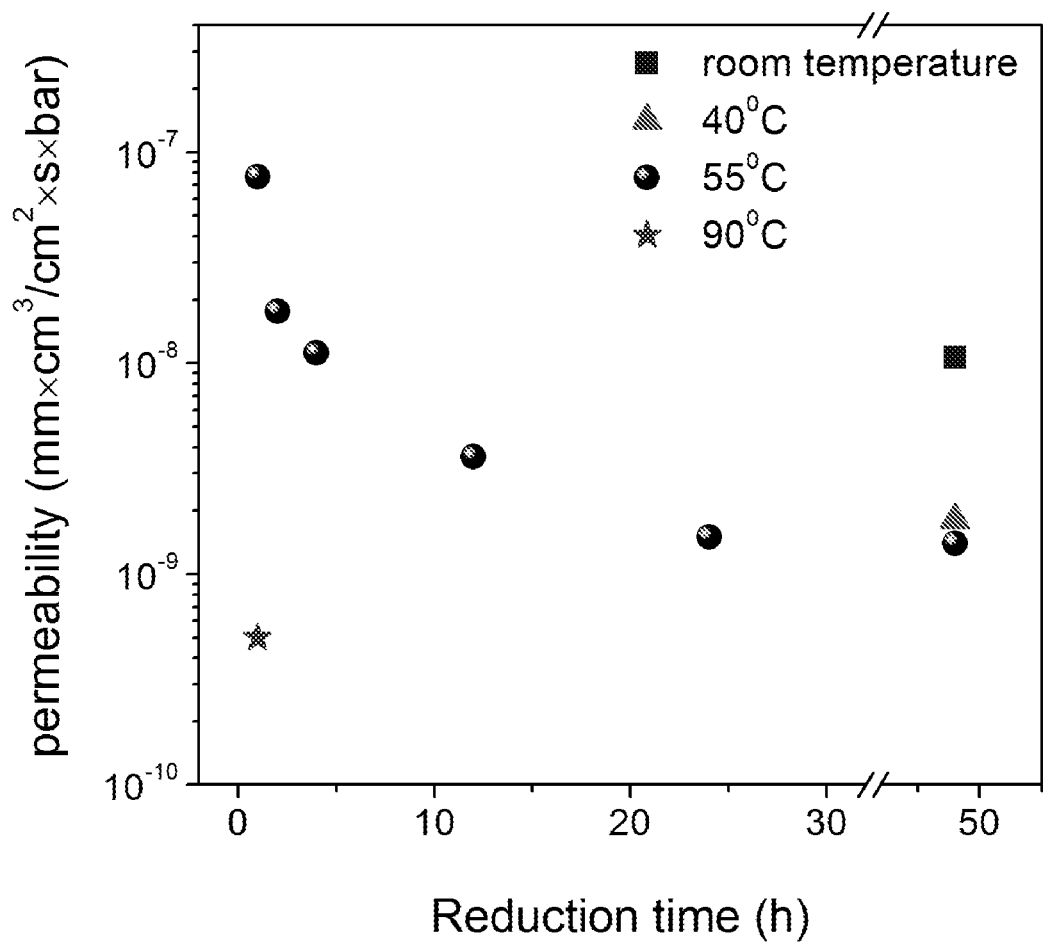
FIG. 7 shows the effect of reduction conditions on the barrier properties of membranes obtained from ascorbic acid reduction.

To study barrier properties of ascorbic acid reduced GO with different reduction conditions, we also performed water permeation experiments with GO reduced with ascorbic acid at different temperatures and also for different reduction time. The results are shown in FIG. 7. FIG. 7 shows ascorbic acid reduction is more efficient above approximately 60° C. The samples reduced below 60° C. shows few times lower water barrier property even after 48 hours of reduction. However, for GO reduced above 60° C., 1 hour reduction is sufficient to obtain good water barrier property.

EXAMPLE 5

Methods of Increasing the Adhesion Between GO and/or rGO Laminate Membranes and Various Substrates Activating PET substrate—PET substrates were cleaned by sonication in ethanol and iso proponal followed by drying with dry nitrogen gas blow. After the cleaning process, the PET substrates were placed under the UV light/ozone for 0.5-2 h for surface activation. Alternatively, PET substrates can be treated by oxygen plasma for 5 min-30 min with a power of 30 W-300 W instead of UV/ozone exposure. During this process the surfaces of the PET get activated with oxygen containing functional groups, which is beneficial for improving the adhesion (due to the improved bonding between GO and PET) and uniformity of the GO/rGO coating on the PET.

Metal surface pre-coating—Pre-coating metal substrates with polymers or molecules is an option to improve the adhesion of GO to metal surfaces. For example, we could spin-coat 20-100 nm thick PMMA on metal surface to improve the adhesion of GO/rGO to the metal.

We have also tested the use of phytic acid as a pre-coating molecule: metal substrates (Steel) were dipped inside phytic acid for 10-60 min and then applied GO coating on top of it. It is believed that phytic acid forms complexes with the atoms on the surface of the metal and Pi-Pi interaction with GO plane, which could improve the adhesion of GO to the metal substrates.

Glass or other silicon based substrates—We have found that sodium metasilicate—GO composite (cross-linked) exhibits good adhesion to glass substrates. Thus, a laminate membrane comprising 60 wt % GO with the remainder sodium metasilicate shows better adhesion to glass substrates than a pure GO laminate.

Example 6

Effect of Mechanical Deformation and Wear on Barrier Properties

Mechanical robustness of barrier films is important for their practical applications. For qualitative assessment of mechanical stability of our rGO films, we have performed He tests for HI-rGO on PET before and after multiple (>10) folding to a radius of less than 1 mm in different directions. FIG. 8a shows an example of our results and compares them with those for the industry-standard films (Al on PET), which experienced the same deformations. The AL film exhibited a 2-3 fold increase in He permeation rates whereas HI-rGO of a similar thickness showed no discernible change. Only films with HI-rGO thickness of ≥200 nm exhibited increased He leaks (see FIG. 8). In this case, the resulting permeation rate were >100 times above our detection limit but still remained significantly lower than the gas permeation through the standard aluminized PET, even before its deformation.

The increased gas permeation after multiple folding for the thicker rGO films can be attributed to their weaker adhesion to PET compared to that of thin coatings. To support this idea, we have performed simple scratch tests on both thin and thick rGO on PET and found that thin (<50 nm) rGO coatings on PET were stable with respect to scratching by a PTFE or wooden sticks whereas thicker films exhibited scratching marks. We believe that, similar to the standard Al films used as gas barriers, the scratchability, adhesion and mechanical robustness could be significantly improved by encapsulating rGO with another thin PET or polymer film.

For further evaluation of the effect of mechanical strain on permeation properties of our barrier films, we have applied an isotropic strain by introducing a differential pressure across PET membranes. The maximum pressure we could apply to our PET films before rupturing them was approximately 4 bars and, therefore, we limited the pressure applied to the barrier films to 2 bars. Membranes were kept under this pressure for 30 minutes and permeation experiments were performed after releasing it. FIG. 8b shows the effect of the strain on bare PET and PET coated with Al and HI-rGO. Bare PET exhibits high He permeation but it changes little before and after applying the strain. The industry-standard aluminized PET became ten times more transparent to He after straining, nearly as transparent as bare PET. This shows that the strain test effectively destroyed the Al film as a gas barrier. Although we have also observed a tenfold increase in He permeation for strained HI-rGO on PET, the permeability remained much lower than for aluminized PET sheets before their straining (FIG. 8).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A barrier material comprising
a reduced graphene oxide laminate membrane; wherein the reduced graphene oxide laminate membrane has a water permeability below $10^{-4}$ g/m$^2$/day at 100% RH and room temperature.

2. The barrier material of claim 1, further comprising an oxidised polymer substrate.

3. The barrier material of claim 2, wherein the oxidised polymer is oxidised poly(ethylene terephthalate) (PET).

4. The barrier material of claim 1, wherein the reduced graphene oxide is formed from the reduction of graphene oxide with a reducing agent which does not generate significant amounts of $CO_2$ or CO as a major component when it reduces graphene oxide; and /or wherein reduction of the graphene oxide with the reducing agent leads to the oxygen originating from the graphene oxide which is displaced being substantially or exclusively expelled as water.

5. The barrier material of claim 1, wherein the reducing agent is one or more selected from the group consisting of: HI, HBr and ascorbic acid (vitamin C).

6. The barrier material of claim 5, wherein the reducing agent is ascorbic acid (vitamin C).

7. The barrier material of claim 1, wherein the reduced graphene oxide laminate membrane is supported on a substrate.

8. The barrier material of claim 7, wherein an adhesion promoter is situated between the reduced graphene oxide laminate and the substrate.

9. The barrier material of claim 8, wherein the substrate is a metal substrate and the adhesion promoter is selected from the group consisting of phytic acid, poly(methyl methacrylate) (PMMA) and polystyrene.

10. The barrier material of claim 8, wherein the substrate is a glass or silicon based substrate and the adhesion promoter is sodium metasilicate.

11. The barrier material of claim 7, wherein the substrate is poly (ethylene terephthalate) (PET).

12. The barrier material of claim 1, wherein a cross-linking agent is interspersed throughout the reduced graphene oxide laminate.

13. The barrier material of claim 12, wherein the cross-linking agent is a polymer.

14. The barrier material of claim 13, wherein the polymer is poly(vinyl alcohol) (PVA).

15. The barrier material of claim 12, wherein the amount of rGO in the laminate is from 30 weight % to 98 weight %.

16. The barrier material of claim 1, wherein the reduced graphene oxide laminate membrane has a water permeability below $10^{-4}$ g/m$^2$/day at 100% RH and room temperature.

17. The barrier material of claim 1, wherein the reduced graphene oxide membrane is affixed to a metal substrate and an adhesion promoter is dispersed throughout the reduced graphene oxide laminate and/or or between the reduced graphene oxide laminate and the substrate.

18. The barrier material of claim 17, wherein the adhesion promoter is a polymer.

19. The barrier material of claim 18, wherein the polymer is poly(vinyl alcohol) (PVA).

20. The barrier material of claim 17, wherein the adhesion promoter is selected from the group consisting of phytic acid, poly(methyl methacrylate) (PMMA), poly(vinyl alcohol) (PVA), polystyrene, poly(4-styrenesulfonate), Nafion, carboxymethyl cellulose, Chitosan, polyvinyl pyrrolidone, and polyaniline.

21. The barrier material of claim 1, wherein the reduced graphene oxide membrane is affixed to a glass or silicon based substrate and an adhesion promoter is dispersed throughout the reduced graphene oxide laminate and/or or between the reduced graphene oxide laminate and the substrate.

22. The barrier material of claim 17, wherein the adhesion promoter is sodium metasilicate.

* * * * *